(12) United States Patent
Raines

(10) Patent No.: US 7,857,805 B2
(45) Date of Patent: Dec. 28, 2010

(54) RATCHETING LUER LOCK CONNECTOR

(75) Inventor: Kenneth Raines, Bethlehem, PA (US)

(73) Assignee: B. Braun Medical Inc., Bethlehem, PA (US)

( * ) Notice: Subject to any disclaimer, the term of this patent is extended or adjusted under 35 U.S.C. 154(b) by 402 days.

(21) Appl. No.: 11/541,717

(22) Filed: Oct. 2, 2006

(65) Prior Publication Data

US 2008/0172039 A1    Jul. 17, 2008

(51) Int. Cl.
*A61M 39/00* (2006.01)
(52) U.S. Cl. ...................................... 604/533
(58) Field of Classification Search .................. 604/533
See application file for complete search history.

(56) References Cited

U.S. PATENT DOCUMENTS

| 5,328,474 | A | 7/1994 | Raines |
| 6,402,207 | B1 | 6/2002 | Segal et al. |
| 6,612,624 | B1 | 9/2003 | Segal et al. |
| 2006/0033331 | A1* | 2/2006 | Ziman ........................ 285/330 |

\* cited by examiner

*Primary Examiner*—Nicholas D Lucchesi
*Assistant Examiner*—Pritesh Patel
(74) *Attorney, Agent, or Firm*—RatnerPrestia

(57) ABSTRACT

According to one aspect of the invention, a fluid carrying connector comprising a luer lock connector is provided. At least one projection is defined on, or extending from, a surface of the luer lock connector. A shroud is moveably positioned with respect to the luer lock connector. The shroud comprises at least one projection that is rotatably positionable with the projection of the luer lock connector. In one rotational direction of the shroud, the projection of the shroud rotates the projection of the luer lock connector in the rotational direction. In an opposite rotational direction of the shroud, the projection of the shroud does not rotate the projection of the luer lock connector in the opposite rotational direction.

29 Claims, 8 Drawing Sheets

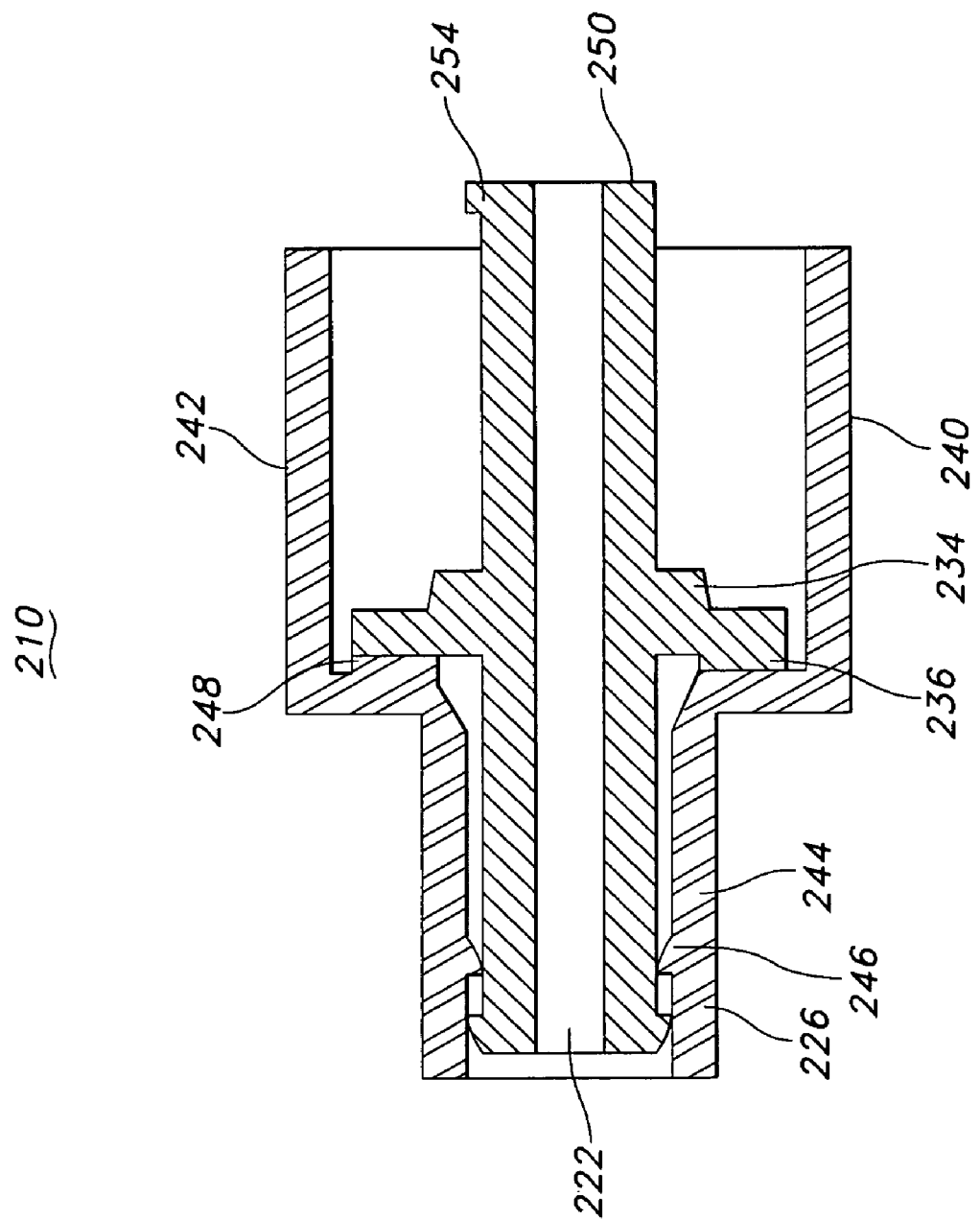

RATCHETING LUER LOCK CONNECTOR

FIELD OF THE INVENTION

The present invention relates to a luer lock connector having a ratcheting shroud for coupling luer lock connectors.

BACKGROUND OF THE INVENTION

In a hospital setting, intravenous fluid is delivered from an infusion source, such as an intravenous (IV) bag, to a patient. In some applications, fluid is delivered through a series of conduits spanning between the infusion source and the patient. More particularly, a fluid delivery conduit, which is connected to the infusion source, is fluidly connected to a fluid receiving conduit which is connected to the patient.

To replace an evacuated infusion source, the fluid delivering conduit is disconnected from the fluid receiving conduit, while the fluid receiving conduit remains connected to the patient. It is typically desirable to leave the fluid receiving conduit, e.g. a catheter, connected to the patient because it may be difficult and time consuming to reconnect the catheter, and may present discomfort to the patient.

Convenient disconnection of the fluid conduits presents an opportunity for narcotics abuse or exposure to hazardous materials, for example. More particularly, if the contents of the IV bag are a narcotic, such as morphine, an individual may disconnect the conduits to withdraw the contents of the IV bag for his or her own unauthorized usage. Furthermore, if the contents of the IV bag are hazardous, such as are chemotherapy fluids, a medical technician or patient may unintentionally disconnect the fluid delivering conduit from the fluid delivering conduit resulting in leakage of the hazardous chemicals. Thus, a need exists to prevent or discourage disconnection of the fluid conduits once interconnected.

SUMMARY OF THE INVENTION

According to one aspect of the invention, a fluid carrying connector comprising a luer lock connector is provided. At least one projection is defined on, or extending from, a surface of the luer lock connector. A shroud is moveably positioned with respect to the luer lock connector. The shroud comprises at least one projection that is rotatably positionable with the projection of the luer lock connector. In one rotational direction of the shroud, the projection of the shroud rotates the projection of the luer lock connector in the rotational direction. In an opposite rotational direction of the shroud, the projection of the shroud does not rotate the projection of the luer lock connector in the opposite rotational direction.

As this invention is not limited to luer lock connectors, according to another aspect of the invention, the fluid carrying connector comprises a fluid delivery conduit defining a fluid passageway therethrough. At least one projection is defined on, or extending from, a surface of the fluid delivery conduit. The shroud is moveably positioned with respect to the fluid delivery conduit. The shroud comprises at least one projection rotatably positionable with the projection of the fluid delivery conduit. In one rotational direction of the shroud, the projection of the shroud rotates the projection of the fluid delivery conduit. In an opposite rotational direction of the shroud, the projection of the shroud does not rotate the projection of the fluid delivery conduit in the opposite rotational direction.

According to still another aspect of the invention, the fluid carrying connector comprises a lock nut positioned over the fluid delivery conduit. At least one projection is defined on, or extending from, a surface of the lock nut. The shroud is movably positioned with respect to the fluid delivery conduit and the lock nut. The shroud comprises at least one projection being positionable with the projection of the lock nut. In one rotational direction of the shroud, the projection of the shroud translates the projection of the lock nut in the rotational direction. In an opposite rotational direction of the shroud, the projection of the shroud does not rotate the projection of the lock nut in the opposite rotational direction.

BRIEF DESCRIPTION OF THE DRAWINGS

The invention is best understood from the following detailed description when read in connection with the accompanying drawing. It is emphasized that, according to common practice, the various features of the drawing may not be shown to scale. Included in the drawing are the following figures:

FIG. 8 is a cross-sectional side view of a female luer lock connector according to yet another exemplary embodiment of the invention.

DETAILED DESCRIPTION OF THE INVENTION

Figure 1:
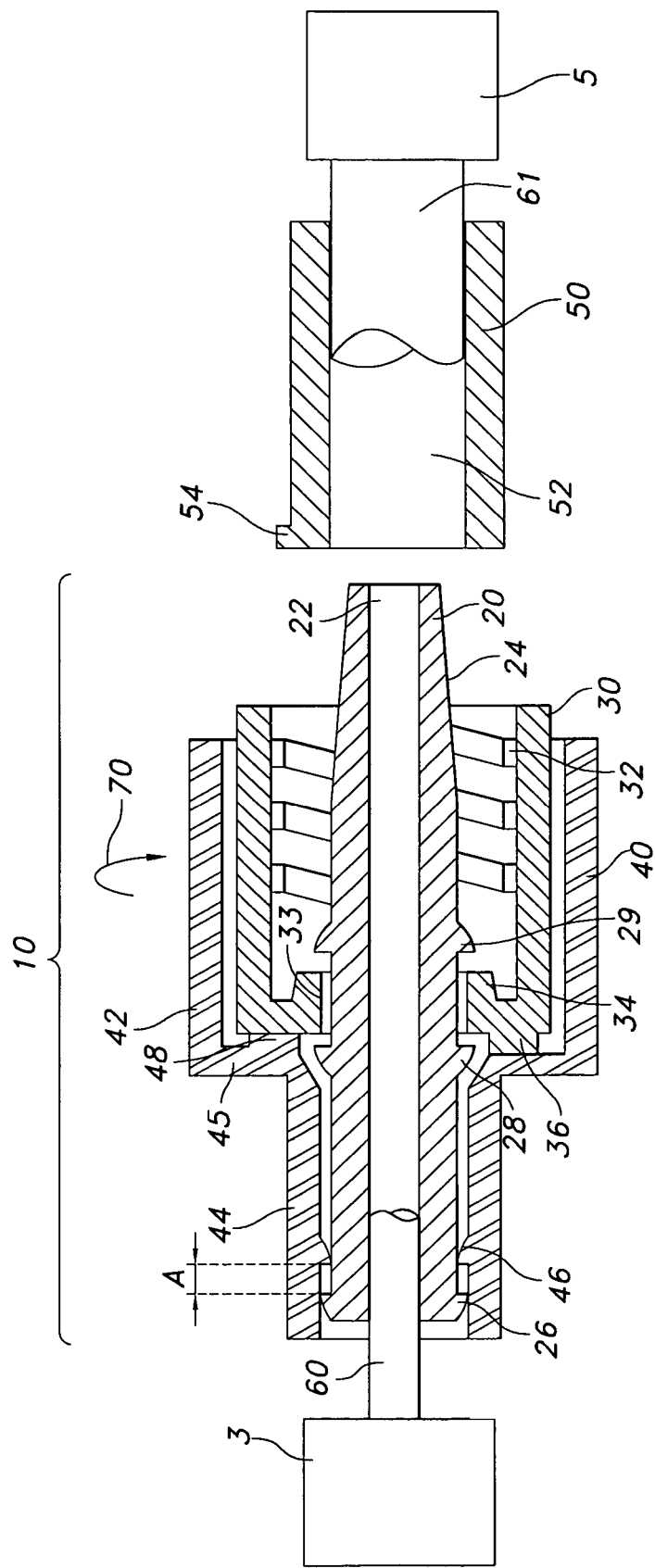
FIG. 1 is a partial block diagram of a fluid delivery system according to an exemplary embodiment of the invention, wherein a cross-sectional side view of a male luer lock connector and a female luer lock connector is illustrated.

The invention will next be illustrated with reference to the Figures. Such Figures are intended to be illustrative rather than limiting and are included herewith to facilitate explanation of the present invention. In the various embodiments, like item numbers represent substantially similar features.

Referring generally to the figures, according to one aspect of the invention, a fluid carrying connector 10, 110, and 210, comprising a luer lock connector 20 & 30, 120 & 130, and 250 is provided. At least one projection 36, 136 and 236 is defined on, or extending from, a surface of the luer lock connector. A shroud 40, 140 and 240 is moveably positioned with respect to the luer lock connector. The shroud comprises at least one projection 48, 148 and 248 that is rotatably positionable with the projection 36, 136 and 236 of the luer lock connector. In one rotational direction of the shroud, the projection 48, 148 and 248 of the shroud rotates the projection 36, 136 and 236 of the luer lock connector in the rotational direction. In an opposite rotational direction of the shroud, the projection of the shroud does not rotate the projection of the luer lock connector in the opposite rotational direction.

Referring now to FIG. 1, a block diagram of a medicinal fluid delivery system is illustrated. The fluid delivery system consists of two tubes 60 and 61 that are interconnected by a pair of male and female luer lock connectors 10 and 50 (the connectors 10 and 50 are not shown in a mated configuration). Tube 60 is connected to an infusion source 3 (shown schematically). The infusion source may represent an IV bag, or other fluid source such as a pump. Tube 61 is connected to the body of a patient 5 (shown schematically).

In one embodiment of the use of this invention, male and female luer lock connectors 10 and 50 are first brought into fluid communication by threadedly coupling male luer lock connector 10 onto female luer lock connector 50. Medicinal fluid is delivered from infusion source 3 through tube 60. Fluid passes through tube 60 into fluid delivery passageway 22 of male luer lock connector 10. Fluid then passes through fluid receiving passageway 52 of interconnected female luer lock connector 50. Fluid then travels through a second tube 61 coupled to female luer lock connector 50. The medicinal fluid is ultimately delivered to patient 5 via tube 61.

Figure 2:
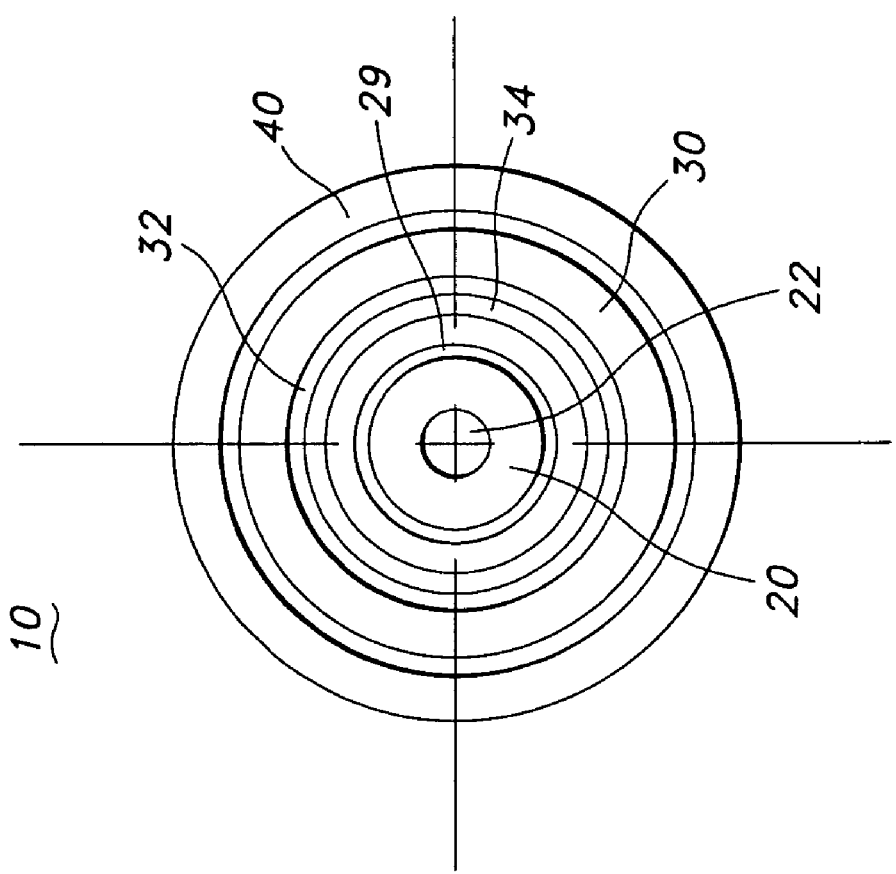
FIG. 2 is a front elevation view of the male luer lock connector of FIG. 1.

FIGS. 1 and 2 illustrate detailed views of male luer lock connector 10, hereinafter connector 10. A cross-sectional side view of connector 10 is shown in FIG. 1, and a front elevation view of connector 10 is shown in FIG. 2. In FIG. 1, female luer lock connector 50 is not shown assembled to connector 10, and is entirely omitted from FIG. 2 for the purpose of clarity. Unlike male luer lock connector 10, female luer lock connector 50 is a standard luer lock connector.

Briefly, male luer lock connector 10 comprises a fluid delivery conduit 20 (commonly referred to as a male luer) defining a fluid flow passageway 22, a floating lock nut 30 rotatably coupled to conduit 20, and a shroud 40 captivated between lock nut 30 and conduit 20. In use, fluid delivery conduit 20 delivers fluid into connector 50, and shroud 40 facilitates threaded connection of lock nut 30 onto connector 50, while discouraging disconnection of lock nut 30 from female connector 50.

One skilled in the art will recognize that the combination of conduit 20 and lock nut 30 of connector 10 resembles a standard male luer lock nut with floating lock nut. For reference, a standard male luer lock connector generally comprises a male luer and a lock nut integrated with the male luer or a floating lock nut rotatably coupled to the male luer. A male luer lock connector may also be referred to in the art as a male luer lock coupler, and the lock nut may also be commonly referred to in the art as a luer lock ring, or lock ring.

The male luer lock connector 10 differs from a standard male luer lock connector in that connector 10 includes a floating shroud 40 that is rotatably coupled between fluid delivery conduit 20 and lock nut 30. A standard male luer lock connector does not include a shroud, such as shroud 40, to facilitate interconnection of male and female luer lock connectors. Furthermore, the conduit 20 and lock nut 30 are uniquely designed for use with shroud 40, as explained in greater detail below.

With reference now to the individual components of connector 10 shown in FIGS. 1 and 2, fluid delivery conduit 20 is a hollow cylindrical body defining a fluid delivery passageway 22 therethrough to facilitate the passage of fluid along its length. The fluid delivery conduit 20 is commonly referred to in the art as a male luer. A fluid carrying tube, such as tube 60, is positioned through the distal end of passageway 22, as shown. A tapered surface 24 is disposed on the exterior surface of the proximal end of conduit 20. The tapered surface 24 is sized to frictionally engage the interior walls of passageway 52 of connector 50 upon insertion, such that fluid may flow between passageways 22 and 52 with little or no leakage.

A series of detents revolved about the exterior surface of fluid delivery conduit 20 are provided to captivate the three components of connector 10 together. Specifically, conduit 20 includes two centrally-located detents 28 and 29, and one detent 26 located at its distal end. In assembled form, flange 34 of lock nut 30 captively floats between the flat surfaces of opposing detents 28 and 29 of conduit 20. The shroud 40 floats between detent 26 of conduit 20 and flange 34 of lock nut 30.

The lock nut 30 is a hollow cylinder rotatably positioned about the proximal end of fluid delivery conduit 20. In the exemplary embodiment shown in FIG. 1, lock nut 30 is separate from conduit 20, such that lock nut 30 may freely rotate independent of conduit 20. By separating lock nut 30 from conduit 20, lock nut 30 may be threaded onto connector 50 without causing rotation of conduit 20. In this fashion, tube 60 does not twist upon rotation of lock nut 30, thereby reducing the potential for detachment of tube 60 from conduit 20. However, as described with reference to the exemplary embodiment illustrated in FIG. 7, the lock nut may be integrated with the fluid delivery conduit.

At the proximal end of lock nut 30, a threaded region 32, in the form of a left-hand helical thread, is formed on the interior surface. The threaded region 32 may also be in the form of a right-hand helical thread. At the distal end of lock nut 30, aperture 33 is provided to accommodate the body of conduit 20 therein. The flange 34 defined along the length of aperture 33 is rotatably positioned between detents 28 and 29 of fluid delivery conduit 20. A series of projections 36 (one shown in FIG. 1), in the form of angled teeth, are formed on the distal surface of flange 34, the purpose of which will be explained with reference to FIGS. 3-6.

The shroud 40 is a hollow cylinder including a large diameter portion 42, a small diameter portion 44, and shoulder 45 extending therebetween. The large diameter portion 42 encapsulates lock nut 30, and small diameter portion 44 encapsulates the distal end of conduit 20. The shroud 40 is sized to encapsulate the length of conduit 20 to discourage a user from grasping conduit 20 or lock nut 30 to disconnect connector 10 from connector 50. For those same reasons, shroud 40 is captivated over the lock nut and conduit 20. A detent 46 revolved about the interior surface of small diameter portion 44, is provided to bear on detent 26 of conduit 20, in order to discourage detachment of shroud 40 from connector 10. A series of projections 48 (one shown in FIG. 1), in the form of angled teeth, are integrally formed on the proximal surface of shoulder 45. In assembly, projections 48 of shroud 40 are positioned to engage projections 36 of lock nut 30. Engagement between projections 48 and projections 36 will be explained in greater detail with reference to FIGS. 3-6.

In assembly of connector 10, lock nut 30 may be assembled onto conduit 20 prior to assembling shroud 40 onto conduit 20, or, alternatively, shroud 40 may be assembled onto conduit 20 prior to assembling lock nut 30 onto conduit 20. The lock nut 30 is assembled onto fluid delivery conduit 20, or vice versa, by pushing flange 34 against the angled surface of detent 29 of conduit 20, until flange 34 flexes sufficiently to permit passage of flange 34 over detent 29. Similarly, shroud 40 is assembled onto fluid delivery conduit 20, or vice versa, by pushing the angled surfaces of detents 46 and 26 together until small diameter portion 44 flexes sufficiently to permit passage of detent 26 over detent 46. Once assembled, it is difficult to disassemble the components of connector 10 without plastically deforming the detents.

To assemble connector 10 onto connector 50, or vice versa, threaded region 32 of lock nut 30 is first aligned with tab 54 of connector 50. Shroud 40 is rotated in a clockwise direction. The projections 48 of shroud 40 engage projections 38 of lock nut 60, causing rotation of lock nut 30. The threaded region of 32 of lock nut 30 then threadedly engages tab 54 of connector 50. Upon rotation of lock nut 30, flange 34 of lock nut 30 bears on detent 29, axially translating conduit 20 into the fluid flow passageway 52 of connector 50, until tapered end 24 of fluid delivery conduit 20 frictionally engages the interior surface of connector 50. It should be understood that while lock nut 30 is fixedly threaded to connector 50 and conduit 20 is firmly seated within connector 50, shroud 40 is not fixed in place and may float between flange 34 and detent 26. The shroud 40 may be thought of as merely a captive tool for fastening connector 10 to connector 50.

Figure 3:
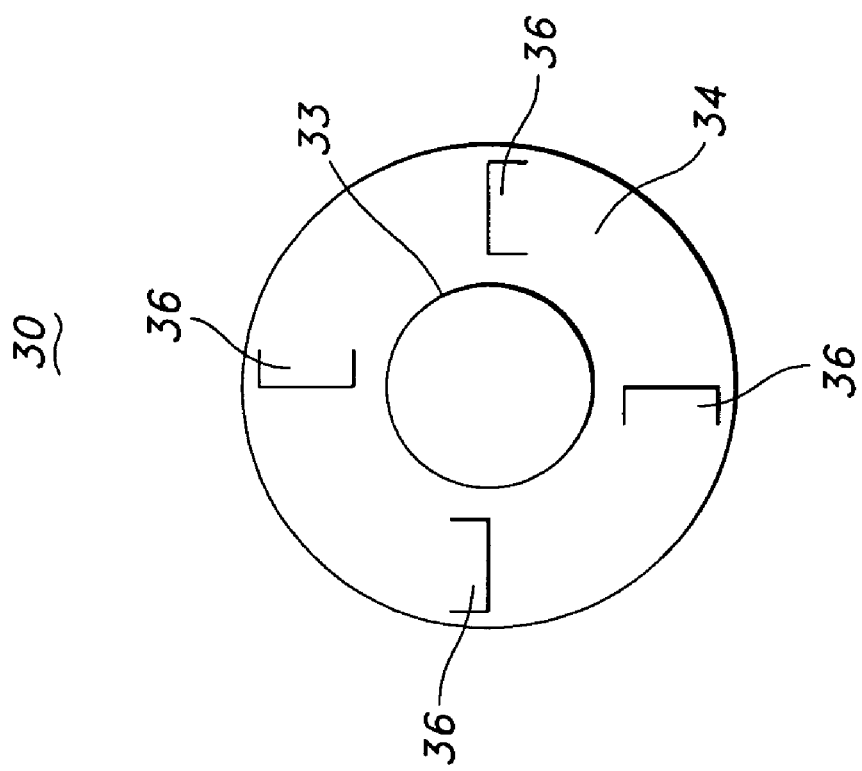
FIG. 3 is a rear elevation view of the lock nut of FIG. 1.
Figure 4:
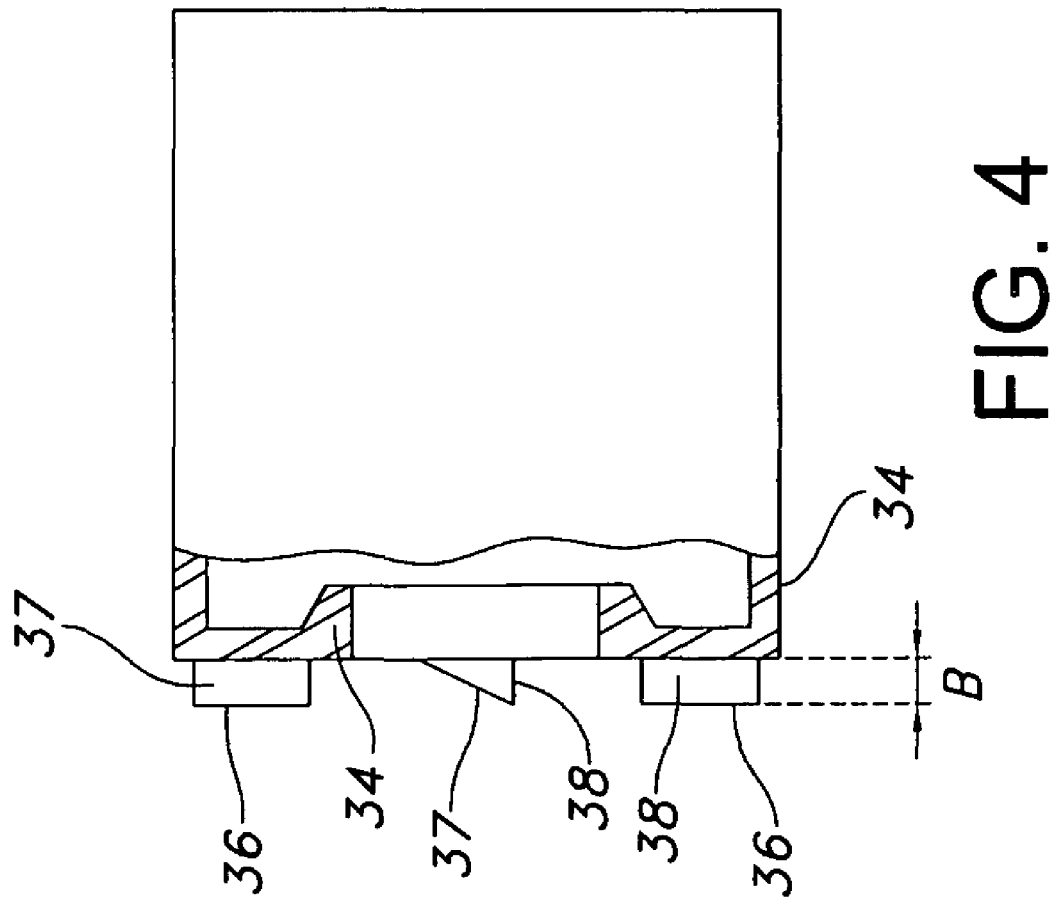
FIG. 4 is a partial cross-sectional side view of the lock nut of FIG. 3.

Referring now to FIGS. 3 and 4, rear elevation and partial cross sectional side views of lock nut 30 are illustrated, respectively. A series of four projections 36 of height "B" extend from the exterior side of flange 34. Although four projections 36 are shown, the lock nut may include any number of projections. Each projection 36 includes an engagement surface 38, and a sliding surface 37 disposed at an angle of less than ninety degrees with respect to engagement surface 38, as best shown in FIG. 4. The projections 36 are each oriented in the same direction about the circumference of lock nut 30. Although not shown, projections 36 may not include a sliding surface.

Figure 5:
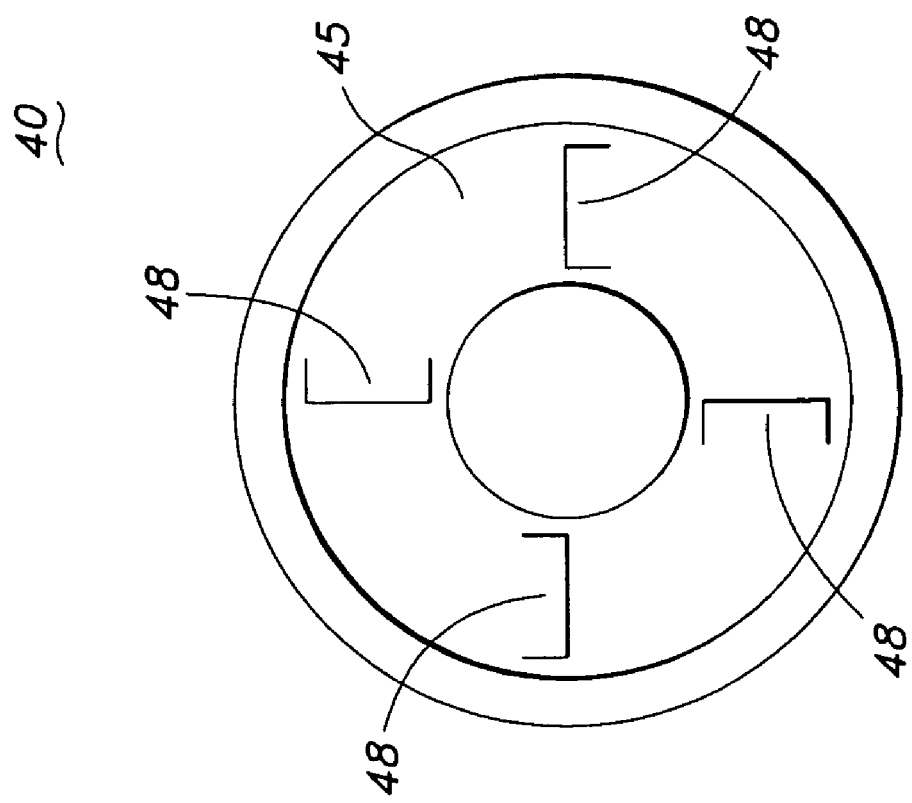
FIG. 5 is a front elevation view of the shroud of FIG. 1.
Figure 6:
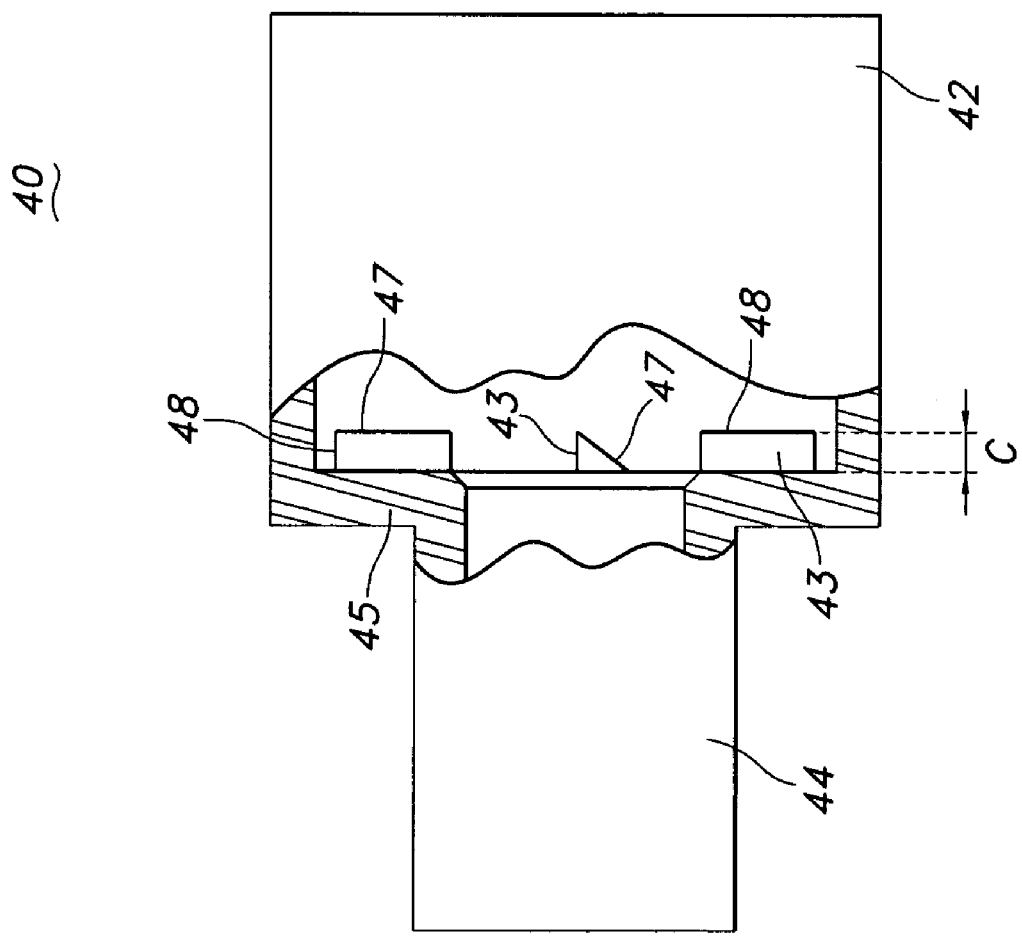
FIG. 6 is a partial cross-sectional side view of a shroud shown in FIG. 5.

Referring now to FIGS. 5 and 6, front elevation and partial cross sectional side views of shroud 40 are illustrated, respectively. A series of four projections 48 extend from the proximal surface of shoulder 45. Although four projections 48 are shown, shroud 40 may include any number of projections. Each projection 48 includes an engagement surface 43 and a sliding surface 47 disposed at an angle of less than ninety degrees with respect to engagement surface 43, as best shown in FIG. 6. The projections 48 are each oriented in the same direction about the circumference of shroud 40. Each of projections 48 have height "C", which may be any dimension smaller than the gap "A" (see FIG. 1). Gap "A" is defined as the axial distance between the engagement surfaces of detents 46 and 26 once flange 34 is abutted against the engagement surface of detent 29 and shroud 40 is in contact with lock nut 30.

Referring back to projections 36 and 48 of connector 10, in an assembled configuration, projections 48 are oriented in the opposite direction of projections 36 of lock nut 30, such that in one rotational direction, the engagement surfaces 38 and 43 of projections 36 and 48 engage each other, and in the opposite rotational direction, the sliding surfaces 37 and 47 of projections 36 and 48 translate over each other. Upon rotation of shroud 40 in the clockwise direction (see arrow 70 in FIG. 1), the engagement surfaces 43 and 38 engage causing lock nut 30 to rotate in a clockwise direction along with shroud 40. Thus, rotation of shroud 40 in the clockwise direction induces clockwise rotation of lock nut 30.

Once connector 10 is connected to connector 50, rotation of shroud 40 in the counterclockwise direction, for example, causes sliding surfaces 47 of projections 48 to contact sliding surfaces 37 of projections 36. Unlike engagement between the engagement surfaces 38 and 43, the sliding surfaces 47 of projections 48 merely translate over sliding surfaces 37 of projections 36, without transferring rotational motion onto the sliding surfaces 37. As the sliding surfaces 37 and 47 translate over each other, shroud 40 axially translates within gap "A" toward detent 26.

It follows that gap "A" should be sufficiently large to permit axial translation of shroud 40 so that sliding surfaces 47 may translate over sliding surfaces 37 of projections 36. It follows that the gap "A" should be greater than height "C" of projections 48, to provide ample clearance for sliding surfaces 47 of projections 48 to translate over sliding surfaces 37 of projections 36. In other words, gap "A" should be set to a dimension greater than height "C", because in a counter clockwise motion, shroud 40 axially translates by a distance equal to height "C" of projections 48. As mentioned above, gap "A" is defined as the axial distance between the engagement surfaces of detents 46 and 26 once flange 34 is abutted against the engagement surface of detent 29 and shroud 40 is in contact with lock nut 30, i.e., a connected configuration.

In summation, once connector 10 is mounted to connector 50, shroud 40 of connector 10 prevents or discourages disconnection of connectors 10 and 50. Because connector 10 may not be disconnected from connector 50 once connected, the possibility of intentional or accidental exposure to the fluids within the fluid delivery system is significantly reduced.

Although not shown, projections 48 or projections 36 may be spring loaded or elastically deformable. In such an embodiment, when the sliding surfaces of projections 48 or projections 36 contact each other, projections 36 and/or 48 would physically compress, such that the sliding surfaces would translate over each other without transferring rotational motion. After the sliding surfaces translate over each other, the projections would immediately return to their original shape or position. In such an embodiment, the size of gap "A" is irrelevant.

Figure 7:
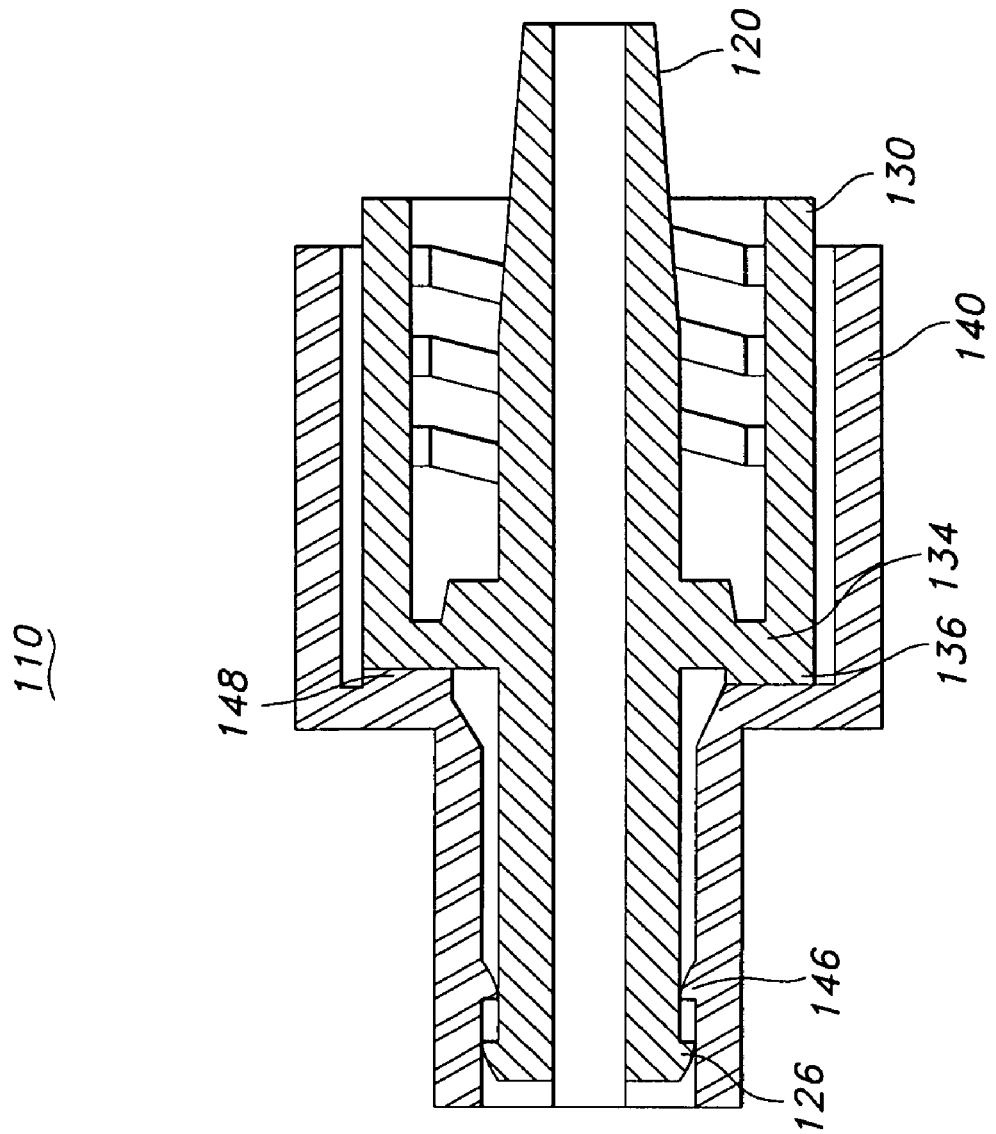
FIG. 7 is a cross-sectional side view of a male luer lock connector according to another exemplary embodiment of the invention.

Alternative exemplary embodiments of the ratchet-style luer lock connector are illustrated in FIGS. 7 and 8. Referring now to FIG. 7, male luer lock connector 110 comprises fluid delivery conduit 120, lock nut 130, and shroud 140. In this exemplary embodiment, lock nut 130 is integrally formed with conduit 120, and shroud 140 is rotatably coupled between conduit 120 and lock nut 130. One skilled in the art will recognize that the combination of fluid delivery conduit 120 and integral lock nut 130 resembles a standard male luer lock connector with integral lock nut. Because lock nut 130 is integrally formed with conduit 120, when connector 110 is rotatably coupled to a female connector (not shown) using shroud 140, conduit 120 rotates along with shroud 140.

Similar to the previous exemplary embodiment, shroud 140 floats between detent 126 of conduit 120 and flange 134 of integral lock nut 130. A series of projections 136 (one shown) are positioned on the distal surface of flange 134. The projections 136 of integral lock nut 130 are positioned to engage complimentary projections 148 (one shown) of shroud 140 in the clockwise direction, for example. In the counterclockwise direction, projections 136 translate over projections 148, translating shroud 140 in an axial direction toward detent 126.

A female version of male luer lock connector 110 is shown in FIG. 8. The female luer lock connector 210 comprises fluid receiving conduit 250 defining a fluid receiving passageway 222 for the passage of fluid. The tab 254 extends from an exterior surface at the proximal end of conduit 250 and is adapted to engage a threaded region of a standard male luer lock connector (not shown). A flange 234 is formed on the medial portion of conduit 250. A series of projections 236 (one shown) are positioned on the distal surface of flange 234. Similar to the previous exemplary embodiments, projections 236 of conduit 250 are positioned to engage complimentary projections 248 (one shown) of shroud 240 in one rotational direction only, e.g. the clockwise direction. Shroud 240 floats between detent 226 and flange 234 of conduit 220.

The connector 210 is configured to be coupled to a conventional male luer lock connector, as opposed to a ratcheting male luer lock connector disclosed herein. In assembly, the lock nut of the male connector (not shown) would reside in the annular space between fluid receiving conduit 250 and shroud 240 of connector 210.

The components of connectors 10, 110 and 210 may be formed from a polymeric material, and molded by an injection molding process, for example. The fluid delivery conduits and the lock nuts may be formed from ABS (i.e., Acrylonitrile Butadiene Styrene), Polycarbonate, Acrylic or any other suitable thermoplastic material. The shroud may be formed from Nylon or Acetyl, for example.

While exemplary embodiments of the invention have been shown and described herein, it will be understood that such embodiments are provided by way of example only. Numerous variations, changes and substitutions will occur to those skilled in the art without departing from the spirit of the invention. For example, although luer lock connectors are shown and described herein, this invention is not explicitly limited to luer lock connectors, as other connector styles are contemplated for use with the invention with slight modification. It should also be understood that the connectors are not limited to the medical industry, as the connectors may used to transfer any noxious chemicals, hot fluids, or cold fluids, for example.

The shape, style and position of the projections may vary. For example, the engageable projections may be positioned on both the interior revolved surface of the shroud and the exterior revolved surface of the lock nut.

Accordingly, it is intended that the appended claims cover all such variations as fall within the spirit and scope of the invention.

What is claimed:

1. A fluid carrying connector that is configured for mating with a mating fluid carrying connector, said fluid carrying connector comprising:
   a luer lock connector;
   at least one projection defined on, or extending from, a surface of said luer lock connector; and
   a shroud moveably positioned with respect to said luer lock connector, said shroud comprising at least one projection rotatably positionable with said at least one projection of said luer lock connector,
   wherein upon rotating the fluid carrying connector onto the mating connector by rotating the shroud in a rotational direction, said at least one projection of said shroud rotates said at least one projection of said luer lock connector in the rotational direction until the luer lock connector of the fluid carrying connector mates with the mating connector, and
   wherein, once the fluid carrying connector is mated with the mating connector, said at least one projection of said shroud is substantially incapable of rotating said at least one projection of said luer lock connector in an opposite rotational direction upon rotating the shroud in the opposite rotational direction, such that the fluid carrying connector is incapable of being unthreaded from the mating connector once mated.

2. The connector of claim 1 wherein in the opposite rotational direction of said shroud, said at least one projection of said shroud translates over said at least one projection of said luer lock connector.

3. The connector of claim 1 wherein said luer lock connector is a male luer lock connector comprising a male luer and a lock nut.

4. The connector of claim 3 wherein said projection of said luer lock connector is defined on a surface of said lock nut.

5. The connector of claim 3 wherein said lock nut is rotatably coupled to said male luer lock connector.

6. The connector of claim 3 wherein said lock nut is integral with said male luer lock connector.

7. The connector of claim 1 wherein said shroud is captivated to said luer lock connector.

8. The connector of claim 1 wherein said luer lock connector is a female luer lock connector.

9. The connector of claim 1, said at least one projection of said shroud further comprising an engagement surface and a sliding surface.

10. The connector of claim 9, said at least one projection of said luer lock connector further comprising an engagement surface, wherein in the rotational direction of said shroud, said engagement surface of said projection of said shroud bears on said engagement surface of said projection of said luer lock connector, rotating said projection of said luer lock connector in the rotational direction.

11. The connector of claim 9 wherein in the opposite rotational direction of said shroud, said sliding surface of said projection of said shroud translates over said at least one projection of said luer lock connector without rotating said at least one projection of said luer lock connector in the opposite rotational direction.

12. The connector of claim 1 wherein said luer lock connector is configured for engagement with another luer lock connector.

13. A fluid carrying connector that is configured for mating with a mating fluid carrying connector, said fluid carrying connector comprising:
   a fluid delivery conduit defining a fluid passageway therethrough;
   at least one projection defined on, or extending from, a surface of said fluid delivery conduit; and
   a shroud moveably positioned with respect to said fluid delivery conduit, said shroud comprising at least one projection rotatably positionable with said at least one projection of said fluid delivery conduit,
   wherein upon rotating the fluid carrying connector onto the mating connector by rotating the shroud in a rotational direction, said at least one projection of said shroud rotates said at least one projection of said fluid delivery conduit in the rotational direction until the fluid delivery conduit of the fluid carrying connector mates with the mating connector, and
   wherein, once the fluid carrying connector is mated with the mating connector, said at least one projection of said shroud is substantially incapable of rotating said at least one projection of said fluid delivery conduit in an opposite rotational direction upon rotating the shroud in the opposite rotational direction, such that the fluid carrying connector is incapable of being unthreaded from the mating connector once mated.

14. The connector of claim 13 wherein said fluid delivery conduit is a male luer.

15. The connector of claim 13 wherein said fluid delivery conduit is a female luer.

16. The connector of claim 13 wherein in the opposite rotational direction of said shroud, said at least one projection of said shroud translates over said at least one projection of said fluid delivery conduit.

17. The connector of claim 13 wherein said shroud is moveably captivated to said fluid delivery conduit.

18. The connector of claim 13, said at least one projection of said shroud further comprising an engagement surface and a sliding surface.

19. The connector of claim 18, said at least one projection of said fluid delivery conduit further comprising an engagement surface, wherein in the rotational direction of said shroud, said engagement surface of said projection of said shroud bears on said engagement surface of said projection of said fluid delivery conduit, rotating said projection of said fluid delivery conduit in the rotational direction.

20. The connector of claim 18 wherein in the opposite rotational direction of said shroud, said sliding surface of said projection of said shroud translates over said at least one projection of said fluid delivery conduit without rotating said at least one projection of said fluid delivery conduit in the opposite rotational direction.

21. A fluid carrying connector that is configured for mating with a mating fluid carrying connector, said fluid carrying connector comprising:
   a fluid delivery conduit defining a fluid passageway therethrough;
   a lock nut positioned over said fluid delivery conduit;
   at least one projection defined on, or extending from, a surface of said lock nut; and
   a shroud movably positioned with respect to said fluid delivery conduit and said lock nut, said shroud comprising at least one projection being positionable with said at least one projection of said lock nut,
   wherein upon rotating the fluid carrying connector onto the mating connector by rotating the shroud in a rotational direction, said at least one projection of said shroud rotates said at least one projection of said lock nut in the rotational direction until the fluid delivery conduit of the fluid carrying connector mates with the mating connector, and
   wherein, once the fluid carrying connector is mated with the mating connector, said at least one projection of said shroud is substantially incapable of rotating said at least one projection of said lock nut in an opposite rotational direction upon rotating the shroud in the opposite rotational direction, such that the fluid carrying connector is incapable of being unthreaded from the mating connector once mated.

22. The connector of claim 21 wherein in the opposite rotational direction of said shroud, said at least one projection of said shroud translates over said at least one projection of said lock nut.

23. The connector of claim 21 wherein said lock nut is integral with said fluid delivery conduit.

24. The connector of claim 21 wherein said lock nut is rotatably coupled to said fluid delivery conduit.

25. The connector of claim 21 wherein said fluid delivery conduit is a male luer.

26. The connector of claim 21, said at least one projection of said shroud further comprising an engagement surface and a sliding surface.

27. The connector of claim 26, said at least one projection of said lock nut further comprising an engagement surface, wherein in the rotational direction of said shroud, said engagement surface of said projection of said shroud bears on said engagement surface of said projection of said lock nut inducing rotation of said projection of said lock nut in the rotational direction.

28. The connector of claim 26 wherein in the opposite rotational direction of said shroud, said sliding surface of said projection of said shroud translates over said at least one projection of said lock nut without rotating said at least one projection of said lock nut in the opposite rotational direction.

29. A fluid carrying connector comprising:
   a lock nut, the lock nut comprising at least one projection, the at least one projection having an engagement surface and a sliding surface; and
   a shroud moveably rotatably positionable with respect to said lock nut, the shroud comprising at least one projection having an engagement surface and a sliding surface;
   the shroud rotatable in a first rotational direction to form a first contact between the engagement surface of the at least one projection of the shroud and the engagement surface of the at least one projection of the lock nut, the first contact imparting torque to the lock nut connector from the shroud; and
   the shroud rotatable in a second rotational direction to form a second contact between the sliding surface of the at least one projection of the shroud and the sliding surface of the at least one projection of the lock nut, the second contact imparting insufficient torque to rotate the lock nut with the shroud.

* * * * *